United States Patent
Watson

(10) Patent No.: US 11,684,438 B2
(45) Date of Patent: Jun. 27, 2023

(54) VISUAL DETECTION OF ELECTROCAUTERY ARCING

(71) Applicant: INTUITIVE SURGICAL OPERATIONS, INC., Sunnyvale, CA (US)

(72) Inventor: Jason Paul Watson, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 660 days.

(21) Appl. No.: 16/642,798

(22) PCT Filed: Aug. 27, 2018

(86) PCT No.: PCT/US2018/048065
§ 371 (c)(1),
(2) Date: Feb. 27, 2020

(87) PCT Pub. No.: WO2019/046152
PCT Pub. Date: Mar. 7, 2019

(65) Prior Publication Data
US 2020/0197072 A1    Jun. 25, 2020

Related U.S. Application Data

(60) Provisional application No. 62/551,635, filed on Aug. 29, 2017.

(51) Int. Cl.
*A61B 18/14* (2006.01)
*A61B 18/12* (2006.01)
(Continued)

(52) U.S. Cl.
CPC ........ *A61B 34/35* (2016.02); *A61B 1/000094* (2022.02); *A61B 18/14* (2013.01);
(Continued)

(58) Field of Classification Search
CPC ........ A61B 2034/305; A61B 2034/306; A61B 34/32–37; A61B 34/70–72;
(Continued)

(56) References Cited

U.S. PATENT DOCUMENTS

| | | | |
|---|---|---|---|
| 4,114,623 A | * | 9/1978 | Meinke .............. A61B 18/1206 606/38 |
| 4,795,253 A | | 1/1989 | Sandridge et al. |

(Continued)

OTHER PUBLICATIONS

International Search Report and Written Opinion for Application No. PCT/US2018/048065, dated Jan. 2, 2019, 13 pages.
(Continued)

*Primary Examiner* — Jaymi E Della
*Assistant Examiner* — Sean W Collins
(74) *Attorney, Agent, or Firm* — Haynes and Boone, LLP

(57) ABSTRACT

Methods and systems for detecting undesirable electrocautery arcing events during an electrocautery surgical procedure may include introducing an electrosurgical treatment instrument to a surgical site to perform an electrocautery surgical procedure. A healthcare provider may view the surgical site with a surgical camera assembly having a surgical field-of-view. The healthcare provider also may view a portion of the electrosurgical treatment instrument with an electrocautery arc detection system including an arc detection camera having an arc detection field-of-view different than the surgical field-of-view obtained by the surgical camera. The electrocautery arc detection system may identify thermal infrared emission or tissue color changes as indicators of undesirable electrocautery arcing. Some implementations alert a healthcare provider of undesirable electrocautery arcing.

20 Claims, 4 Drawing Sheets

(51) Int. Cl.
*A61B 34/35* (2016.01)
*A61B 90/00* (2016.01)
*A61B 1/00* (2006.01)
*A61B 34/00* (2016.01)
*A61B 18/16* (2006.01)
*A61B 17/00* (2006.01)
*A61B 18/00* (2006.01)

(52) U.S. Cl.
CPC ........ *A61B 90/361* (2016.02); *A61B 1/00193* (2013.01); *A61B 18/16* (2013.01); *A61B 2017/00119* (2013.01); *A61B 2017/00199* (2013.01); *A61B 2018/00595* (2013.01); *A61B 2018/00982* (2013.01); *A61B 2018/1253* (2013.01); *A61B 2034/741* (2016.02); *A61B 2034/742* (2016.02)

(58) Field of Classification Search
CPC .................. A61B 18/14; A61B 90/361; A61B 2017/00119; A61B 2018/00595; A61B 2018/00982
See application file for complete search history.

(56) References Cited

U.S. PATENT DOCUMENTS

| | | |
|---|---|---|
| 5,762,609 A | 6/1998 | Benaron et al. |
| 2003/0225401 A1 | 12/2003 | Eggers et al. |
| 2007/0108990 A1 | 5/2007 | Oguchi et al. |
| 2009/0024023 A1* | 1/2009 | Welches ............... A61B 90/361 |
| | | 600/549 |
| 2012/0083779 A1 | 4/2012 | Hosier et al. |
| 2012/0088965 A1* | 4/2012 | Stokes ............... A61B 1/00087 |
| | | 600/104 |
| 2018/0168734 A1* | 6/2018 | Strobl .................... A61B 34/20 |
| 2019/0254737 A1* | 8/2019 | Fischer ............. A61B 18/1233 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2018/048065, dated Mar. 12, 2020, 9 pages.

* cited by examiner

VISUAL DETECTION OF ELECTROCAUTERY ARCING

CROSS-REFERENCE TO RELATED APPLICATIONS

This application is the U.S. national phase of International Application No. PCT/US2018/048065, filed Aug. 27, 2018, which designated the U.S. and claims the benefit of U.S. Provisional Application 62/551,635 filed Aug. 29, 2017, all of which is are incorporated by reference herein in its their entirety.

TECHNICAL FIELD

The present disclosure is directed to systems utilized in medical procedures and operational methods used during those procedures. More particularly, the present disclosure is directed to systems and methods of detecting electrocautery arcing during a medical procedure.

BACKGROUND

Medical robotic systems such as teleoperational systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical teleoperational systems is strong and growing.

Examples of medical teleoperational systems include the da Vinci® Surgical System and the da Vinci® S™ Surgical System from Intuitive Surgical, Inc., of Sunnyvale, Calif. Each of these systems includes a health care provider's console, a patient-side cart, a high performance three-dimensional ("3-D") vision system, and Intuitive Surgical's proprietary EndoWrist® articulating instruments, which are modeled after the human wrist. When added to the motions of manipulators holding the surgical instruments, these articulating instruments allow at least six degrees of freedom of motion to their end effectors, which is comparable to or even greater than the natural motions of open surgery.

Electrosurgical treatment instruments are used by medical teleoperational systems to treat patient tissue using heat produced by electrical energy. As electrical current is conducted through the tissue, the target tissue temperature rises, ultimately causing desiccation, cutting, cauterization, and/or coagulation of the target tissue. Such electrocautery instruments provide significant utility in minimally invasive surgical procedures. However, as with any surgical instrument, and with any surgical procedure, there is always the chance of unexpected effects. With respect to electrocautery, unintentional current leakage may occur under certain circumstances, such as the use of damaged or expired instruments, or the exceeding of recommended power inputs, among others. Such current leakage may result in tissue cauterization away from the surgical site and/or damage to the surgical instrument/system.

Minimally invasive surgical procedures performed by teleoperational systems provide many advantages over conventional surgery, however as the size of access points are reduced, so is visualization of the surgical site. Accordingly, conventional systems may not provide ideal visualization beyond the specific and narrow region of tissue to be treated during the surgical procedure. Because of this, unintended current leakage, such as electrocautery arcing (e.g., discharge of electrical energy), from portions of surgical instruments or cameras may be not visually detectable though a surgical camera utilized to drive the surgical procedure. These discharges can result in thermal damage to bodily tissues, resulting in chronic and acute complications.

To increase the likelihood of detecting electrocautery arcing, it would be desirable to provide an arc detecting camera at the surgical site to observe the surgical tools utilized during electrocautery surgical procedures.

SUMMARY

In general, the present disclosure is directed to systems and methods for observing a surgical scene with a perspective that is more expensive than the visual field of the surgeon's view. The observed surgical scene may include portions of the surgical instruments, camera, and accessories that may contact or be in close proximity to the patient. From this viewpoint, it may be possible to observe unintended cautery discharge. Additional certain embodiments of the invention are best summarized by the claims that follow the description.

Some exemplary aspects of the present disclosure are directed to methods of detecting an arc during in an electrocautery surgical procedure. The method may include viewing an electrosurgical treatment instrument having an electrocautery distal tip and a surgical site with a surgical camera having a surgical field-of-view including the surgical site. The method also may include viewing a portion of the electrosurgical treatment instrument with an electrocautery arc detection system for detecting thermal infrared emission or tissue color changes. The electrocautery arc detection system may include an arc detection camera having an arc detection field-of-view different than the surgical field-of-view obtained by the surgical camera.

Additional exemplary aspects of the present disclosure may include methods of detecting an arc during in an electrocautery surgical procedure that may include introducing an electrosurgical treatment instrument to a surgical site. The electrosurgical treatment instrument may have an electrocautery tip configured to perform a surgical procedure and a shaft portion supporting the electrocautery tip. The method may include displaying a surgical video stream from a surgical camera assembly having a first field-of-view of the surgical site. The surgical video stream may include an image of the electrocautery tip. An arc detecting video stream may be monitored from an arc detection camera having a second field-of-view larger than the first field-of-view. The arc detection camera may be disposed to view portions of the electrosurgical treatment instrument not visible in the first field-of-view.

In yet additional exemplary aspects, the present disclosure may be directed to systems for detecting an arc during an electrocautery surgical procedure at a surgical site. The systems may include an electrosurgical treatment instrument having a working tip configured to perform a surgical procedure and may include a surgical camera having a field-of-view of the surgical site. The system also may include an arc detecting camera having a field-of-view different than the field-of-view of the surgical camera.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

DETAILED DESCRIPTION

Figure 1A:
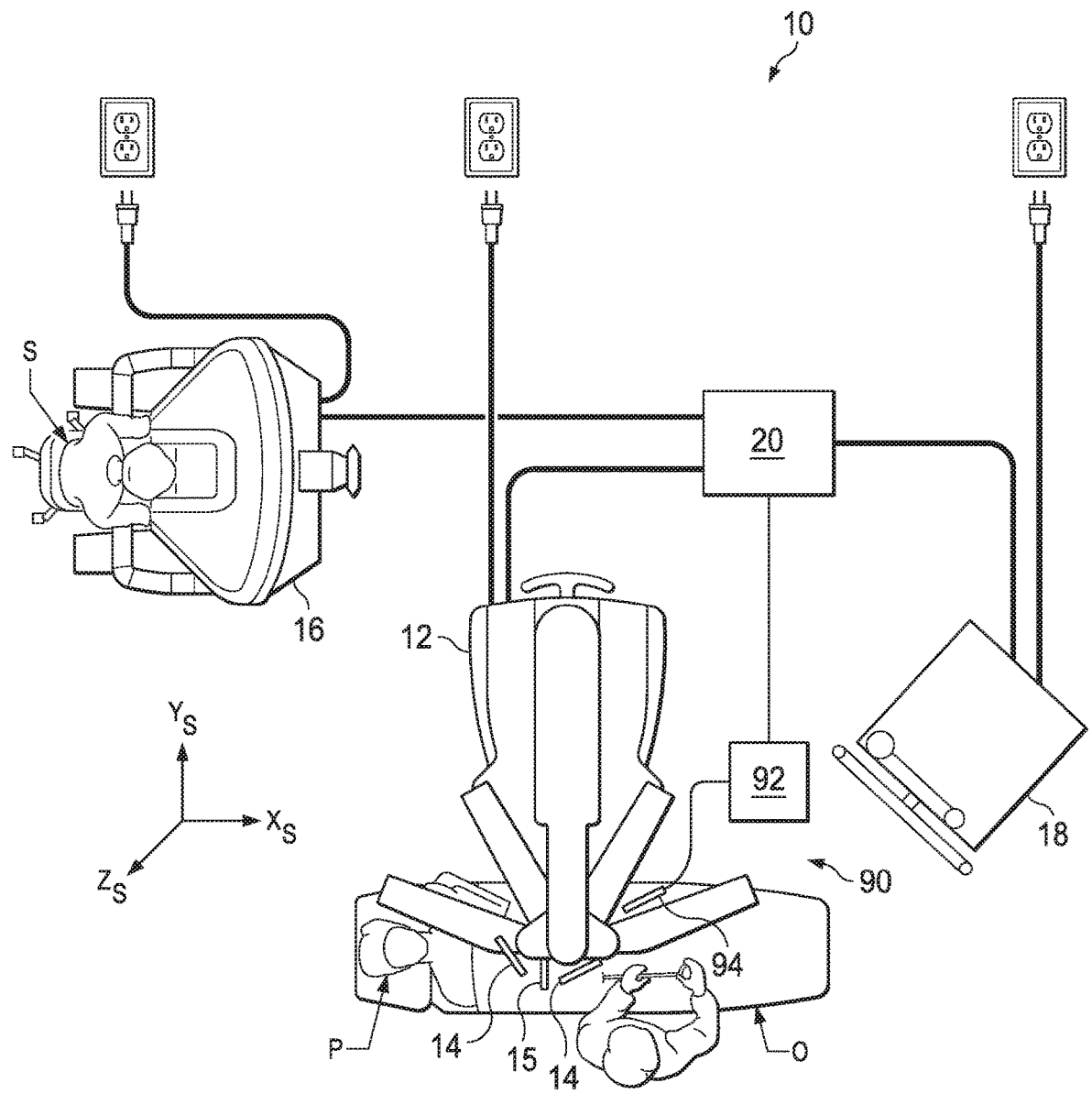
FIG. 1A is a schematic view of a teleoperated medical system in a surgical frame of reference, in accordance with an embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as to not unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Referring to FIG. 1A of the drawings, a teleoperated medical system for use in, for example, medical procedures including diagnostic, therapeutic, or surgical procedures, is generally indicated by the reference numeral 10 and operates within a surgical environment having a surgical frame of reference coordinate system, XS, YS, ZS. As will be described, the teleoperated medical systems of this disclosure are under the teleoperated control of a health care provider. In alternative embodiments, a teleoperated medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1A, the teleoperated medical system 10 generally includes a teleoperated assembly 12 mounted to or near an operating table O on which a patient P is positioned. The teleoperated assembly 12 may be referred to as a patient side cart. A medical instrument system 14 and an endoscopic imaging system 15 are operably coupled to the teleoperated assembly 12. An operator input system 16 allows a surgeon or other type of health care provider S to view images of or representing the surgical site and to control the operation of the medical instrument system 14 and/or the endoscopic imaging system 15. An electrocautery arc detection system 90 including an image processing controller 92 and an arc detecting camera 94 may be used with the medical instrument system 14 and endoscopic imaging system 15 as will be described below. Together with the patient side cart, the electrocautery arc detection system 90 may be known as or may form a part of a patient side system. The endoscopic imaging system 15 provides images of the external surfaces of anatomic structures within the surgical environment. The electrocautery arc detection system 90 may be an internal imaging system capable of imaging internal surgical tools as well as internal surfaces of anatomical structures.

The operator input system 16 may be located at a health care provider's console, which is usually located in the same room as operating table O. It should be understood, however, that the health care provider S can be located in a different room or a completely different building from the patient P. The health care provider's operator input system 16 includes left and right eye displays for presenting the health care provider S with a coordinated stereo view of the surgical site that enables depth perception. The operator input system 16 further includes one or more input control devices which cause the teleoperated assembly 12 to manipulate one or more instruments or the endoscopic imaging system. The input control devices can provide the same degrees of freedom as their associated surgical tools to provide the health care provider S with telepresence, or the perception that the input control devices are integral with the surgical tools so that the health care provider has a strong sense of directly controlling the surgical tools. To this end, position, force, and tactile feedback sensors (not shown) may be employed to transmit position, force, and tactile sensations from the instruments back to the health care provider's hands through the input control devices. The control device(s) may include one or more of any number of a variety of input devices, such as hand grips, joysticks, trackballs, data gloves, trigger-guns, hand-operated controllers, voice recognition devices, touch screens, body motion or presence sensors, and the like. In some embodiments, the control device(s) will be provided with the same degrees of freedom as the medical instruments of the teleoperated assembly to provide the health care provider with telepresence, the perception that the control device(s) are integral with the instruments so that the health care provider has a strong sense of directly controlling instruments as if present at the surgical site. In other embodiments, the control device(s) may have more or fewer degrees of freedom than the associated medical instruments and still provide the health care provider with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The teleoperated assembly 12 supports and manipulates the medical instrument system 14 while the health care provider S views the surgical site through the console of the operator input system 16. An image of the surgical site can be obtained by the endoscopic imaging system 15, such as a stereoscopic endoscope, which can be manipulated by the teleoperated assembly 12 to orient the endoscope of the endoscopic imaging system 15. An electronics cart 18 can be used to process the images of the surgical site for subsequent display to the health care provider S through the health care provider's console of the operator input system 16. The number of medical instrument systems 14 used at one time will generally depend on the diagnostic or surgical procedure and the space constraints within the operating room among other factors. The teleoperated assembly 12 may include a kinematic structure of one or more non-servo controlled links (e.g., one or more links that may be manually positioned and locked in place, generally referred to as a set-up structure) and a teleoperated manipulator. The teleoperated assembly 12 includes a plurality of motors that drive inputs on the medical instrument system 14. These motors move in response to commands from the control system (e.g., control system 20). The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument for grasping tissue in the jaws of a biopsy device or the like.

The teleoperated medical system 10 also includes a control system 20. The control system 20 includes at least one memory and at least one processor (not shown), and typically a plurality of processors, for effecting control between the medical instrument system 14, the endoscopic imaging system 15, the operator input system 16, and monitors on the electronics cart 18. The control system 20 may also receive and process images from the electrocautery arc detection system 90. The electronics cart 18 may house components of the endoscopic imaging system 15, the electrocautery arc detection system 90, the control system 20 as well as monitor and processors for processing and displaying captured images.

The control system 20 also includes programmed instructions (e.g., a computer-readable medium storing the instructions) to implement some or all of the methods described in accordance with aspects disclosed herein. While control system 20 is shown as a single block in the simplified schematic of FIG. 1A, the system may include two or more data processing circuits with one portion of the processing optionally being performed on or adjacent the teleoperated assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperated systems described herein. In one embodiment, control system 20 supports wireless communication protocols such as Bluetooth, IrDA, HomeRF, IEEE 802.11, DECT, and Wireless Telemetry.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing teleoperated assembly 12 to move the medical instrument system(s) 14 and/or endoscopic imaging system 15 which extend into an internal surgical site within the patient's body via openings in the body. Any suitable conventional or specialized servo controller may be used. A servo controller may be separate from, or integrated with, teleoperated assembly 12. In some embodiments, the servo controller and teleoperated assembly are provided as part of a teleoperated arm cart positioned adjacent to the patient's body.

Figure 4:
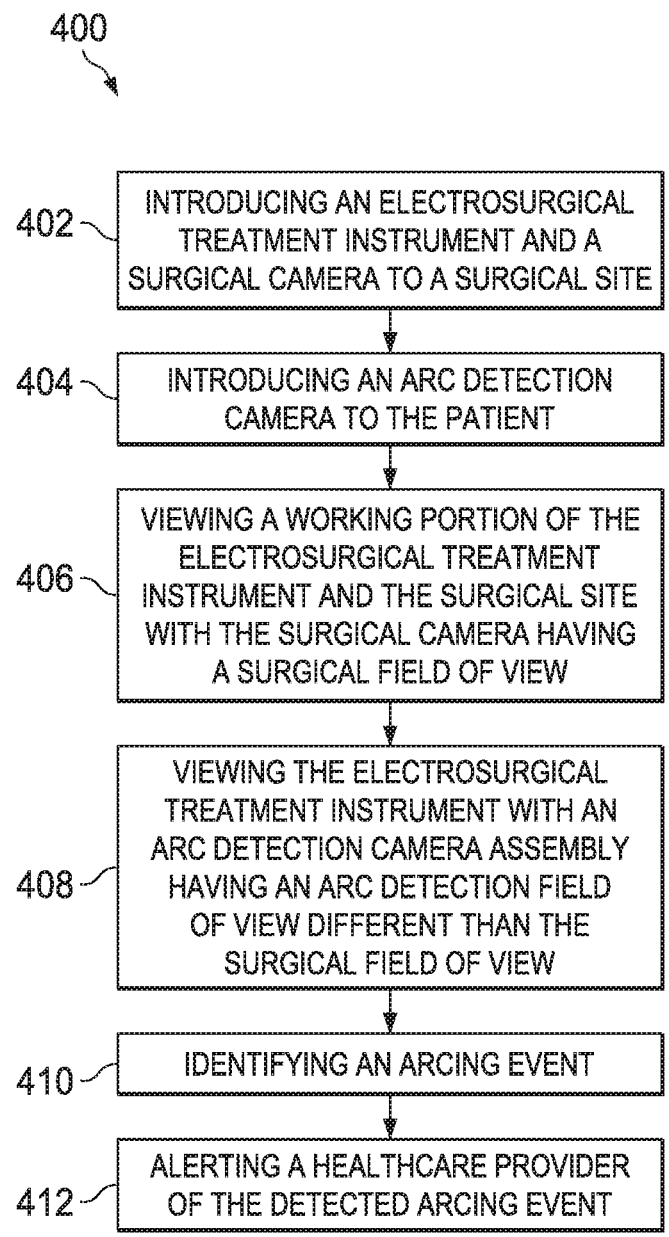
FIG. 4 is a simplified flow diagram of a method of identifying an electrocautery event during a medical procedure according to some embodiments.

Some examples of processors may include non-transient, tangible, machine readable media that include executable code that when run by one or more processors may cause the one or more processors to perform the processes or methods described herein, including the method 400 of FIG. 4. Some common forms of machine readable media that may include the processes of methods herein are, for example, floppy disk, flexible disk, hard disk, magnetic tape, any other magnetic medium. CD-ROM, any other optical medium, punch cards, paper tape, any other physical medium with patterns of holes, RAM, PROM, EPROM, FLASH-EPROM, any other memory chip or cartridge, and/or any other medium from which a processor or computer is adapted to read.

The teleoperated medical system 10 may further include optional operation and support systems (not shown) such as illumination systems, steering control systems, irrigation systems, and/or suction systems. In alternative embodiments, the teleoperated system may include more than one teleoperated assembly and/or more than one operator input system. The exact number of manipulator assemblies will depend on the surgical procedure and the space constraints within the operating room, among other factors. The operator input systems may be collocated, or they may be positioned in separate locations.

Figure 1B:
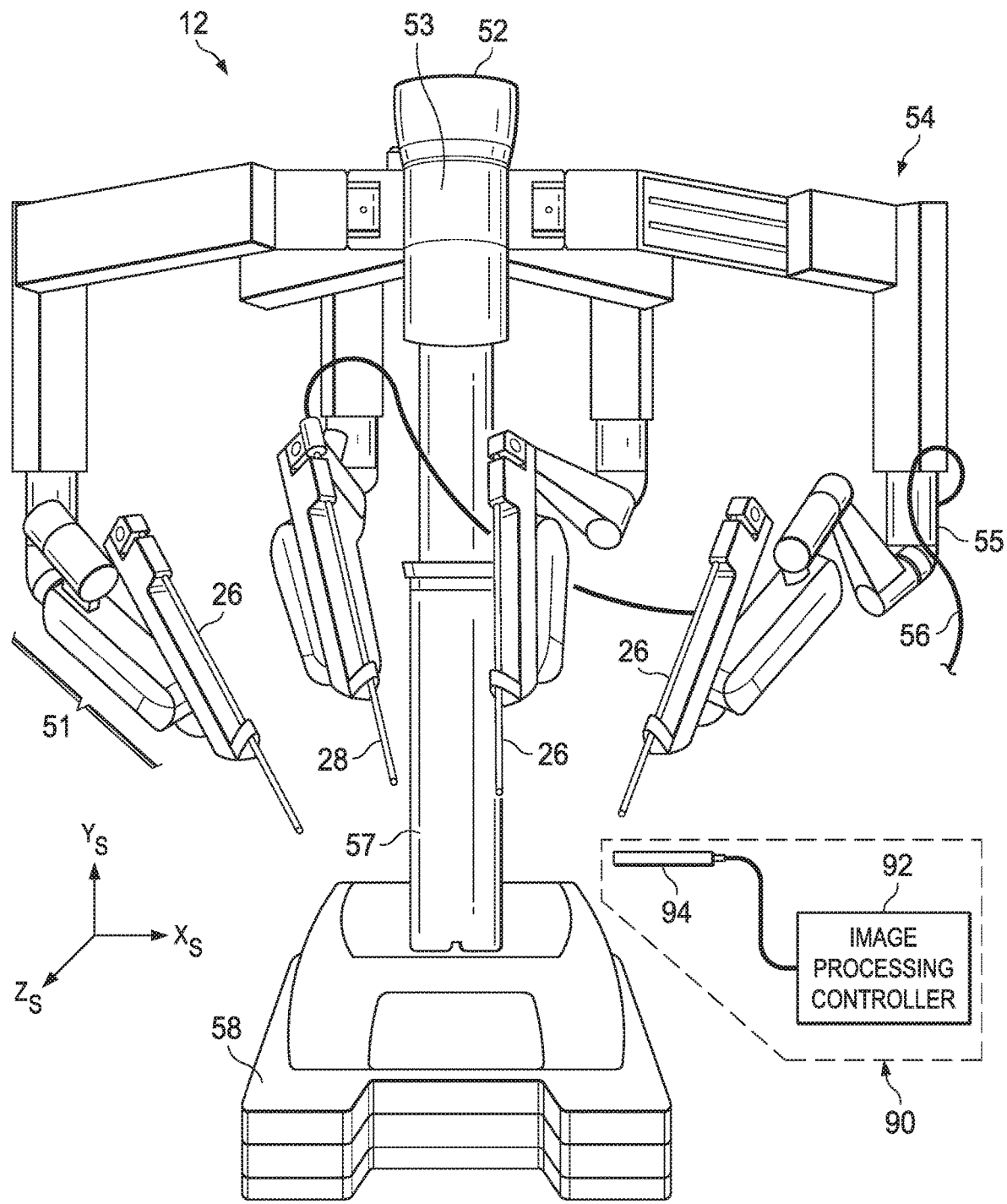
FIG. 1B is a perspective view of patient side systems, according to one example of principles described herein.

FIG. 1B is a perspective view of one embodiment of a teleoperated assembly 12 and a block diagram of an electrocautery arc detection system 90. The teleoperated assembly 12 shown provides for the manipulation of three surgical tools 26 (e.g., instrument systems 14) and an imaging device 28 (e.g., endoscopic imaging system 15), such as a stereoscopic endoscope used for the capture of images of the site of the procedure. As used herein, the term capture or captured images is intended to include still shots, video, and streaming. The imaging device may transmit signals over a cable 56 to the electronics cart 18. Manipulation is provided by teleoperative mechanisms having a number of joints. The imaging device 28 and the surgical tools 26 can be positioned and manipulated through incisions or natural orifices in the patient so that a kinematic remote center is maintained at the incision to minimize the size of the incision. Images of the surgical site can include images of the distal ends of the surgical tools 26 when they are positioned within the field-of-view of the imaging device 28.

The teleoperated assembly 12 includes a drivable base 58. The drivable base 58 is connected to a telescoping column 57, which allows for adjustment of the height of the arms 54. The arms 54 may include a rotating joint 55 that both rotates and moves up and down. Each of the arms 54 may be connected to an orienting platform 53. The orienting platform 53 may be capable of 360 degrees of rotation. The teleoperated assembly 12 may also include a telescoping horizontal cantilever 52 for moving the orienting platform 53 in a horizontal direction.

In the present example, each of the arms 54 connects to a manipulator arm 51. The manipulator arms 51 may connect directly to surgical tools 26. The manipulator arms 51 may be teleoperable. In some examples, the arms 54 connecting to the orienting platform are not teleoperable. Rather, such arms 54 are positioned as desired before the health care provider begins operation with the teleoperative components.

The electrocautery arc detection system 90 may be arranged to identify unintended discharge of electrical energy from portions of surgical instruments that are outside the typical surgical view of the imaging device 28. The electrocautery arc detection system 90 includes the image processing controller 92 and the arc detecting camera 94 to provide the electrocautery arc detection. The arc detecting camera 94 may be a minimally invasive instrument sized for insertion into the surgical environment. The electrocautery arc detection system 90 and the arc detecting camera 94 are discussed in greater detail below with reference to FIGS. 2-4.

Endoscopic imaging systems (e.g., systems 15, 94, and/or 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" camera design in which a distal digital sensor such as a one or more charge-coupled device (CCD) or a complementary metal oxide semiconductor (CMOS) device acquire image data. Endoscopic imaging systems may provide two- or three-dimensional images of the endoscopic field-of-view (i.e. the imaging area) to the viewer. Two-dimensional images may provide limited depth perception. Three-dimensional stereo endoscopic images may provide the viewer with more accurate depth perception. Stereo endoscopic instruments employ stereo cameras to capture stereo images of the field-of-view of the patient anatomy. An endoscopic instrument may be a fully sterilizable assembly with the endoscope cable, handle and shaft all rigidly coupled and hermetically sealed.

Figure 2:
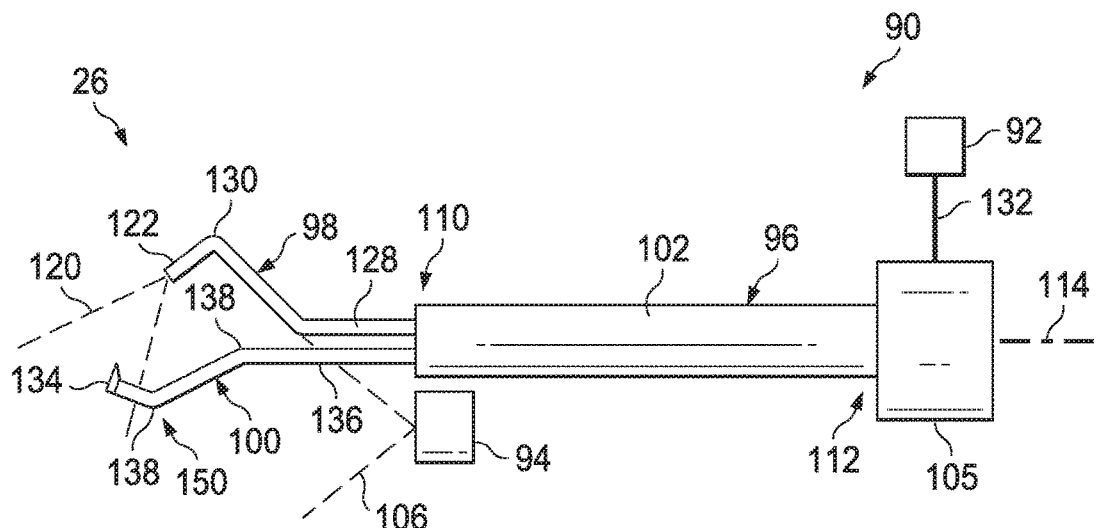
FIG. 2 is a simplified illustration of an electrocautery arc detection system with surgical tools for a single port surgical procedure according to some embodiments.

FIG. 2 is a simplified illustration of an example electrocautery arc detection system 90 including the image processing controller 92 and the arc detecting camera 94, along with an access cannula 96 and a pair of surgical tools 26, identified in this example as a surgical camera 98 and an electrosurgical treatment instrument 100. In this implementation, the electrocautery arc detection system 90 is configured to be used in a single port surgery. As indicated above, the electrocautery arc detection system 90 may be incorporated into a teleoperational medical system such as the teleoperated medical system 10 shown in FIGS. 1A and 1B. In other implementations, the electrocautery arc detection system 90 may be used independently of the teleoperated medical system depicted in FIGS. 1A and 1B. For example, the electrocautery arc detection system 90 may be used in standalone and/or manually operated applications.

In this embodiment configured for single port surgery, the arc detecting camera 94 is carried by the access cannula 96. The arc detecting camera 94 may be any of a plurality of camera types, including for example a standard digital camera capable of capturing still or streamed images, an infrared thermal imaging camera identifying changes in tissue temperatures in the electromagnetic spectrum, a filter processing camera arranged to detect arcing that can accompany unintended discharge, or other type of camera or camera system. In some implementations, the arc detection camera 94 may be a thermal infrared camera arranged to monitor thermal infrared emission. Therefore, the arc detection camera may include sensors and optics suited for those wavelengths, such as HgCdTe-based photo sensors and ZnSe optics. In other implementations, the arc detecting camera 94 and optics may have filters which enhance the visibility of electrical arcs. In some examples, the filters may be chosen to block the wavelength bands where the surgical light source emits. As such, the bulk of the light which falls on the sensors of the arc detecting camera would have originated from a cautery event. In some examples, filtering, such as by the image processing controller 92, could also be applied to the video stream coming from the camera. In some implementations, the arc detecting camera 94 may cooperate with the image processing controller 92 to identify when an arcing event has occurred or is occurring. In some implementations, the arc detecting camera 94 includes a wide-angle lens allowing the arc detecting camera 94 to have a field-of-view 106 that is broader than merely the surgical site to be treated, and includes at least some portion of the surgical tools 26 that are not encompassed or visual from the surgical camera. In some implementations, the wide-angle lens has a field of view of at least 45 degrees. In some implementations, the wide-angle lens has a field of view of at least 67 degrees, and in some implementations, the wide-angle lens has a field of view of at least 90 degrees. Accordingly, the wide angle lens may have a field of view in ranges of 45 to 120 degrees, 65 to 95 degrees, 80 to 100 degrees, and in other ranges.

The image processing controller 92 is configured to receive images as either still images or as a datastream from the arc detecting camera 94. The image processing controller 92 may include a processor and memory, and in some implementations, may form a part of the control system 20 of the teleoperated medical system 10. The image processing controller 92 may receive and process incoming data to identify hotspots, arcing, or other detrimental activities that can occur during an electrocautery arcing occurrence. Accordingly, the image processing controller 92 may be configured with executable instructions for carrying out processes to identify the hotspots, arcing or other detrimental activities. For example, in one implementation, image processing controller 92 may be configured to receive data representing a thermal infrared light detected by the arc detecting camera 94 and identify the location and magnitude of any unintended discharge of electrical energy into patient tissue. For example, the image processing controller 92 may monitor the captured image from the arc detecting camera 94 and may identify hotspots based on color or temperature changes detected by the arc detecting camera. In some implementations, the image processing controller 92 may, either independently or in cooperation with the control system 20, generate alerts or take action to minimize tissue to that could result from prolonged electrocautery arcing. In another implementation, the image processing controller 92 may be configured to receive data representing a filtered image to identify when an arcing event occurs.

In some implementations, the image processing controller 92 may communicate any image obtained by the arc detecting camera 94 to the operator input system 16 so that the operator may view the field-of-view 106 from the architect and camera 94.

In this implementation, the arc detecting camera 94 is carried on the access cannula 96. The access cannula 96 includes a main body 102 and an optional hub 105. The main body 102 is formed as a hollow tube having a distal end 110 and a proximal end 112, and having a lumen passing therethrough from the distal end 110 to the proximal end 112. In the implementation shown, the main body 102 is formed as a cylinder defining and extending along an axis 114. The main body 102 may be insertable into the body of the patient for the delivery or removal of fluid, gathering of data, or providing access to instruments or surgical tools inserted through the lumen. Although the diameter of the main body 102 may vary, some implementations include a range of about 14 to 24 gauge. Other sizes are contemplated. In addition, the main body 102 may have any length sufficient to provide access to the desired region of the patient. In some implementations, the length of the main body may be within a range of about 1 inch to 12 inches, although other lengths, both larger and smaller, are contemplated.

The hub 105 may be disposed at the proximal end 112 of the main body 102. The hub 105 may be a flange or collar having a diameter greater than the diameter of the main body 102. In some implementations, the hub 105 may act as a mechanical stop that prevents the access cannula 96 from moving distally further into a patient. In some implementations, the hub 105 may be disposed a specific or known distance from the distal end 110 of the main body so that a health care provider is immediately aware of a depth of the distal end 110 of the main body 102 when the hub 105 abuts against the patient's body or other mechanical stop. In some implementations, the hub 105 may be a connector connectable to tubes or other components or systems usable during the surgery.

The surgical tools 26 in this implementation include the surgical camera 98 and the electrosurgical treatment instrument 100. The surgical tools 26 may extend through the lumen of the access cannula 96 to treat internal tissue of the patient. The surgical tools may be standard tools known in the art, and each poses some risk of undesired electrocautery arcing. The surgical camera 98 may be the endoscope imaging device 28 forming a part of the endoscopic imaging system 15 in FIGS. 1A and 1B. The surgical camera 98 may be a rigid or flexible endoscope and may be sized for insertion through the access cannula 96 to the surgical site and may extend out of the distal end 110 of the access cannula 96. In some implementations, the surgical camera 98 may provide a direct video feed through the control system 20 to the operator input system 16. The live video feed from the surgical camera 98 may be displayed to the health care provider at the operator input system 16. By observing the live video feed on the display, the health care provider may perform the surgical procedure. In order to provide the level of detail and precision necessary for performing the surgical procedure, the surgical camera 98 may have a field-of-view 120 originating from a distal end 122 of the surgical camera 98. The field-of-view 120 may be arranged to be primarily directed at and encompass the tissue being treated as well as a tissue treating end of the electrosurgical treatment instrument 100. Through the surgical camera 98, the healthcare provider performing the surgical procedure may be able to view the surgical procedure in process and make decisions and control the electrosurgical treatment instrument 100 via the operator input system 16.

In addition to being able to capture images of the surgical site, the surgical camera 98 may have a body, referred to as a shaft 128 having one or more elbows, joints, or curves 130 that during use may be disposed in close proximity to tissue in the body. In some implementations, these elbows, joints, or curves 130 may be formed at wrist-like mechanisms provided between the distal end 122 of the surgical camera 98 and the lumen of the access cannula 96. In other implementations, these elbows, joints, or curves 130 may be simply rigid elbows that create a protruding portion. The surgical camera 98 may include a surgical light source that illuminates the surgical area so that healthcare providers may better visualize the feed from the surgical camera 98. In some implementations, the surgical light source may be disposed at a location separate and apart from the surgical camera 98, while in some implementations, the surgical light source is integrated with or adjacent to the surgical camera 98.

The electrosurgical treatment instrument 100 may be capable of treating tissue with the use of heat produced by electrical energy. For example, the electrosurgical treatment instrument may include a working tip, such as a cautery hook or electrode 134 that applies current to tissue at the surgical site. Depending upon the implementation, the electrosurgical treatment instrument 100 may comprise a combined cutting, shearing, clamping, stapling, or grasping electrosurgical instrument. As the current flows through the tissue, the tissue temperature rises, ultimately causing desiccation, cutting, cauterization, and or coagulation of the target tissue. The electrosurgical treatment instrument 100 includes a body, referred to as a shaft 136 having one or more elbows joints or curves 138 that during use, may be disposed in close proximity of tissue in the body. In some implementations, the elbows, joints, or curves 138 may be motorized servo controlled joints or telescoping elements that may displace in the patient's body to move the electrode 134 to desired positions to carry out the treatment process. Although shown only extending from the distal end of the access cannula 96, the shaft 136 of the electrosurgical treatment instrument 100 may extend entirely through the lumen of the access cannula 96. In some implementations, the electrosurgical treatment instrument 100 may be controlled or manipulated via the teleoperated assembly 12. In the following, the electrosurgical circuit is configured in a monopolar setup, with a return electrode on the patient (as opposed to a bipolar setup, in which both electrodes are located at the distal end of the instrument). The electrosurgical treatment instrument 100 also may be susceptible to unintentional current leakage into nearby tissue. That is, cautery current may unintentionally leak from the electrocautery supply conductor that delivers the electrical energy to the electrode 134 during the treatment procedure. For example, any metal portions of the instrument shaft that enclose the electrocautery supply conductor will form a capacitor. Electrocautery current will leak across this capacitor if the metal portions of the shaft come in contact with tissue. Again, this problem may be magnified if fluids, such as blood or saline, enter or seep into an interior of an instrument shaft that houses the conductor, and in some instances, may cause increased capacitive coupling between the instrument shaft and the patient resulting in unintended current being imparted to the patient. A similar situation can occur when an instrument configured to delivery electrocautery energy touches metal portions, e.g., the end effector of a second instrument, which may or may not be configured to deliver electrocautery energy. Additionally, during the application of electrocautery energy, the electrical potential between the patient and earth ground may differ significantly from zero. The shafts of endoscopes are typically connected to earth ground, and if the endoscope shaft is not connected to the patient as well, for example when a plastic port reducer is used, then harmful leakage current can be produced if the endoscope shaft touches a small area of the patient. Leakage of cautery current caused by capacitive coupling is undesirable as it may cause unnecessary and unintended burning of the patient from the shaft 136. Although monopolar setups are described, the principles described herein also find utility with bipolar setups.

FIG. 2 identifies potential arc locations along the shaft 136 of the electrosurgical treatment instrument 100. In this implementation, the potential arc locations 150 correspond to the elbows, joints, or curves 138 on the shaft 136 of the electrosurgical treatment instrument 100. In other implementations, the potential arc locations 150 may be disposed at locations other than the elbows joints or curves of the shaft 130. In order to provide sufficient access to the surgical site with the surgical tools 26 and with the necessary close-up viewing of the tissue treated at the surgical site, the field-of-view 106 from the surgical camera 98 typically excludes the elbows, joints, or curves on the shaft of a surgical tool, such as the electrosurgical treatment instrument 100. Instead, the field-of-view 106 from the surgical camera 98 is typically focused on the distal, tissue-treating tip, which in FIG. 2 is the electrode 134 of the electrosurgical treatment instrument 100. Therefore, because the surgical camera field-of-view 120 is focused on the surgical site, the surgical camera field-of-view 120 typically does not encompass the potential arc locations 150.

Here, the arc detecting camera 94 is disposed in a position to provide a field-of-view 106 that includes the shaft 136 of the electrosurgical treatment instrument 100, including elbows, joints, or curves 138 on the shaft 136 of the electrosurgical treatment instrument 100. The field-of-view 106 of the arc detecting camera 94 may also include the shaft 128 of the surgical camera 98 and its elbows, joints, or curves 130. In some implementations including the implementation in FIG. 2, the field-of-view 106 of the arc detecting camera 94 is wider than the field-of-view of the surgical camera 98. As such, it shows more of the surgical tools themselves and it may show tissue adjacent shafts of one or more of the surgical tools 26. Because of this, undesired electrocautery events that occur outside the field-of-view of the surgical camera 98, may still be captured or visualized by the arc detecting camera 94. In some implementations, the arc detecting camera 94 may be spaced from the electrode 134 and tissue treated by the electrode 134 in a manner that the arc detecting camera 94 by itself may be insufficient to provide the detail and focus needed of the surgical site. That is, the surgical camera 98 may have a focus and view sufficiently suited for the surgical site but not for arc detection, and the arc detecting camera 94 may have a focus and view sufficiently suited for arc detecting, but not for controlling surgical tools at the surgical site. In some implementations, the arc detecting camera 94 may be unsuitable for operation as a surgical camera because it may be configured to identify flashes of light or heat detection, but not configured to provide a suitable stream for viewing tissue and performing a surgical procedure.

In FIG. 2, the arc detecting camera 94 is disposed adjacent to and outside of the distal end 110 of the access cannula 96. Accordingly, the arc detecting camera 94 abuts against or is provided at an external surface of the access cannula 96. In other implementations, the arc detecting camera 94 may be disposed elsewhere relative to the distal end 110 of the access cannula 96. For example, an arm or physical structure may space the arc detection camera 94 away from the external surface of the access cannula 96 to provide a field-of-view that includes shafts and potential arc locations of the surgical tools 26 when they are manipulated or disposed in positions different than the position shown in FIG. 2.

In the implementation shown, the access cannula 96 is connected to the image processing controller 92 via a cable 132. The cable 132 may extend to the arc detecting camera 94 and may be arranged to carry data signals from the arc detecting camera 94 to the image processing controller 92. As indicated above, the image processing controller 92 may be in communication with or may form a part of the control system 20 of the teleoperated medical system 10 (FIG. 1A). In some implementations, the image processing controller 92 may be disposed on the access cannula 96 with the arc detecting camera 94. In some implementations, the arc detecting camera 94 includes a light detector or image sensor, while the image processing occurs at the image processing controller 92. In other implementations, the camera 124 includes the light detector or image sensor and the processor and memory functions to enable the camera to capture images. The cable 132 may also carry commands to the arc detecting camera 94. For example, if the arc detecting camera 94 is capable of an optical zoom, then control signals from the health care provider to the arc detecting camera 94 may be carried by the cable 132. In some implementations, the cable 132 may extend down the lumen of the main body 102, may be embedded in the wall of the main body 102, or may be otherwise situated to physically connect the arc detecting camera 94 to the image processing controller 92. In some implementations, the arc detecting camera 94 includes or is in communication with a wireless transmitter or transceiver that may transmit or stream signals of captured images to the image processing controller 92 for storage or display to the health care provider. The surgical camera 98 and the electrosurgical treatment instrument 100 may connect to the teleoperated assembly 12 in manners known in the art.

Figure 3:
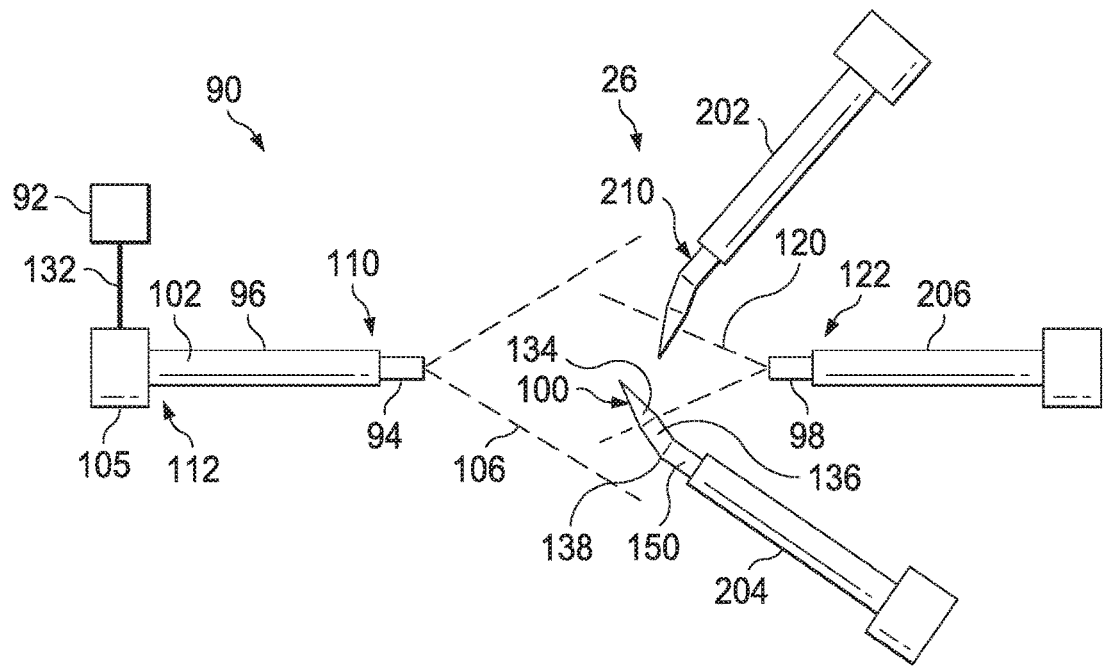
FIG. 3 is a simplified illustration of an electrocautery arc detection system with surgical tools for a multi-port surgical procedure according to some embodiments.

FIG. 3 is a simplified illustration of an example electrocautery arc detection system 90 in a multi-port surgery arrangement. The electrocautery arc detection system 90 includes the image processing controller 92 and the arc detecting camera 94, along with an access cannula 96 and a pair of surgical tools 26. However, in this instance, the arc detecting camera 94 is mounted ahead of the surgical field of the surgery. FIG. 3 includes the access cannula 96 providing access for the arc detection camera 94. However, because FIG. 3 is an example of a multiport surgery arrangement, the additional access cannulas 202, 204, 206 provide access to the surgical field. The access cannulas 202, 204,

206 are similar to the access cannula 96 described with reference to FIG. 2, and therefore will not be re-described in detail.

In this implementation, the arc detecting camera 94 extends through the lumen and out the distal end 110 of the access cannula 96. Accordingly, FIG. 3 shows the arc detection camera 94 in line with the access cannula 96. The arc detecting camera 94 may be any arc detecting camera described herein.

The access cannula 202 may extend through another port in the patient's body toward the surgical site and may accommodate any of a plurality of surgical tools that may treat the surgical site. For example, FIG. 3 shows a surgical instrument 210 extending through the access cannula 202 for treating tissue at the surgical site. The surgical instrument 210 may be configured to treat tissue at a surgical site by cutting, shearing, clamping, stapling, or grasping, for example. In some implementations, the surgical instrument 210 is an electrosurgical treatment instrument, while in other implementations, the surgical instrument 210 is a different type of instrument. As described herein, so long as at least one of the surgical instruments 210 is configured to deliver monopolar cautery, then the potential for arcing exists for all the surgical instruments 210.

The access cannula 204 may extend through another port in the patient's body toward the surgical site and may accommodate any of a plurality of surgical tools that may treat the surgical site. In this implementation, the surgical tool extending through the access cannula 204 may be the electrosurgical treatment instrument 100. As described with reference to FIG. 2, the electrosurgical treatment instrument 100 may include an electrode 134 at its distal tip and may perform operations such as for cutting, shearing, clamping, stapling, or grasping, or others. In order to manipulate either the distal end of the electrosurgical treatment instrument or tissue at the distal end of the electrosurgical treatment instrument, the electrosurgical treatment instrument 100 includes the shaft 136, which may include elbows, joints, or curves 138 in the manner described herein. These elbows, joints, or curves may create potential arc locations 150 as described herein.

FIG. 3 shows the surgical camera 98 extending through the access cannula 206. In the implementation shown, the access cannula 206 provides access to the surgical site for only the surgical camera 98. The surgical camera 98 is intended to provide a streaming image of the surgical site so that the healthcare provider can control or manipulate the surgical instrument 210 and the electrosurgical treatment instrument 100 to perform a desired procedure on tissue at the surgical site. Accordingly, the surgical camera 98 provides the surgical field-of-view 120 focused on tissue treated at the surgical site and the tips or active ends of the surgical tools in contact with the tissue. As described with reference to FIG. 3, the surgical camera field-of-view 120 is narrow in order to provide suitable detail of the surgical site. It also excludes the shaft 136 of the electrosurgical treatment instrument 100, including any elbows, joints, or curves 138 on the shaft 136 of the electrosurgical treatment instrument 100. In so doing, it also excludes the potential arc locations 150.

By comparison, the arc detection camera 94 has a field-of-view 106 that includes the potential arc locations 150. That is, the field-of-view 106 may provide visual coverage of the shaft 136, the elbows joints or curves 138 of the electrosurgical treatment instrument 100. It may also provide visual coverage of a shaft with elbows joints or curves of the surgical instrument 210. In this instance, the field-of-view 106 of the arc detection camera 94 is larger or wider than the surgical field-of-view 120 of the surgical camera 98. In addition, its location relative to the surgical site may provide better visualization of the surgical tools 26 than of the tissue being treated by the surgical tools. In the implementation shown in FIG. 3, the field-of-view 106 from the arc detection camera 94 is wide enough to provide visualization of the entire tea of the surgical instruments extending from the distal tip of their respective access cannulae 202, 204.

FIG. 4 is a simplified diagram of a method 400 for detecting an arc during electrocautery surgical procedure. According to some embodiments, the method 400 may be performed using, for example, the teleoperated medical system 10 as described herein. The method may begin at 402 by introducing an electrosurgical treatment instrument and a surgical camera to a surgical site. Depending on the implementation, this may include advancing each of the electrosurgical treatment instrument and the surgical camera through an access cannula to the surgical site. In some implementations, this may include advancing both the electrosurgical treatment instrument and the surgical camera through the same access cannula. In other implementations, this may include advancing the electrosurgical treatment instrument and the surgical camera through separate and independent access cannulae.

At 404, the health care provider may introduce an arc detection camera to the patient. This may include advancing an arc detection camera through a cannula to the surgical site at an angle or field-of-view different than that obtained by the surgical camera. In some implementations, introducing an arc detection camera to the patient may occur at the same time the access cannula is introduced to the patient. For example, in a single port surgical procedure, the arc detection camera may be disposed on the access cannula when the access cannula is introduced to the surgical site. In other examples, including in single port surgical procedures, the arc detection camera may be introduced to the surgical site after the access cannula is introduced to the patient. The arc detection camera may be arranged provide a wider field-of-view than the surgical camera. In some implementations, the arc detection camera may be arranged to monitor thermal infrared emission. Therefore, the arc detection camera may need sensors and optics suited for those wavelengths. In other implementations, the arc detecting camera and optics may have filters which enhance the visibility of electrical arcs. In some examples, the filters may be chosen to block the wavelength bands where the surgical light source emits. As such, the bulk of the light which falls on the sensors of the arc detecting camera would have originated from a cautery event. In some examples, filtering, such as by the image processing controller 92, could also be applied to the video stream coming from the camera.

At 406, the health care provider may view a working portion of the electrosurgical treatment instrument and the surgical site with the surgical camera having a surgical field-of-view. The working portion of the electrosurgical treatment instrument may include a distal tip that is configured to interface with patient tissue at the surgical site. In some instances, this may include the electrode 134 configured to perform an electrocautery procedure. The surgical field-of-view may also be arranged and focused on tissue being treated. Typically, it is this view that a health care provider may see while performing a surgical procedure. This also may typically be the view presented to the healthcare provider at the operator input system 16 controlling the teleoperated medical system 10. The surgical field-of-view typically does not include the shaft and any elbows, joints, or curves of the shaft extending from the access cannula. Rather, the surgical field-of-view typically includes a visualization of the tissue and the working tips of the associated surgical tools.

At 408, the method includes viewing the electrosurgical treatment instrument with an arc detecting camera assembly having an arc detection field-of-view different than the surgical field-of-view. Because the fields-of-view are different, the arc detecting field-of-view may be directed at or include the entire or portions of shafts of the surgical tools performing procedures at the surgical site. For example, the arc detection field-of-view may provide visualization or may be wide enough to include elbows, joints, or curves on shafts of the electrosurgical treatment instrument or other surgical tools. The arc detection field-of-view may be arranged to provide visualization or coverage of potential arc locations on the surgical tools. In addition, it may cover or provide visualization of areas of the surgical tools that are not visible in the surgical camera field-of-view obtained by the surgical camera. That is, the surgical field-of-view from the surgical camera may be suited for viewing the surgical site but not suitable for arc detection, and the arc detecting camera may suited for arc detecting, but not for controlling surgical tools by viewing the tissue and tips of surgical tools at the surgical site. In some implementations, the arc detecting camera 94 may be unsuitable for operation as a surgical camera because it may be configured to identify flashes of light or heat detection, but not a suitable stream for viewing tissue and performing a surgical procedure.

In some implementations of the method, viewing the electrosurgical treatment instrument with an arc detecting camera may include viewing the electrosurgical treatment instrument and tissue adjacent the body, shaft, elbows, joints, or curves on the shaft. As indicated above, in implementations where the arc detection camera is sensitive to radiation in the thermal infrared portion of the electromagnetic spectrum, increases in temperature at locations where unintended arcing events may occur can be directly detected. In additional implementations of the method, viewing electrosurgical treatment instrument with an arc detecting camera may include viewing filtered or processed imagery in such a way as to emphasize and detect arcing that can accompany unintended discharge. As indicated herein, this may include image processing that includes identifying flashes or strobes of light in it video or datastream.

At 410, the method may include identifying an arcing event. In implementations using an arc detection camera sensitive to radiation in the thermal infrared portion of the electromagnetic spectrum, identifying an arcing event may include identifying when temperature of tissue increases while streaming an image or data of the tissue and portions of the electrosurgical treatment instrument. In some instances, identifying when temperature of tissue increases may occur automatically, when the image processing controller identifies a temperature change based on the data or image provided by the arc detecting camera. Accordingly, in some instances, identifying an arcing event may include identifying changes in color of a video stream. This may include identifying when tissue temperature exceeds a set threshold temperature. Based upon the changes monitored by the arc detecting camera and from the thermal infrared feedback, the electrocautery arc detection system may be able to identify not only the location of the arcing event, but also the magnitude or temperature change on the tissue. In other instances, identifying when the temperature of tissue increases may occur manually or visually by a healthcare provider watching a display showing a thermal infrared stream from the arc detecting camera.

In implementations using filtered or processed imagery at 410, identifying an arcing event may include monitoring the video stream for flashes of light at cautery frequencies or wavelengths. In some examples, light generated by surgical light sources may be filtered out, but may leave light that may be generated by a cautery or arcing event. In such instances, a flash of light may be indicative of an arcing event. In some examples, cautery frequencies are typically between 500 kHz, which is well below the pixel data rate of a 60 Hz high definition camera. This means that the temporal signature of a cautery arc could be captured in the pixel data, even if not visible to the naked eye. Processing may include monitoring the video stream in time and monitoring for flashes or strobes of light at the cautery frequency or wavelengths.

In some implementations, since the arc detecting camera (which includes imaging or processing occurring at the image processing controller 92) may be arranged to provide infrared images or filtered imaging that would not be visually suitable to a health care provider controlling surgical tools to perform a surgical procedure based on the imaging, the arc detecting camera and the surgical camera may be arranged to capture different types of images.

At 412, the teleoperated medical system alerts a healthcare provider to the cautery event. In implementations where the image processing controller 92 automatically processes and identifies the location, magnitude, or more generally, the occurrence, of an arcing event, the image processing controller may alert the healthcare provider to the cautery event. In some implementations, this may include a visually notifying the health care provider on a display of the operator input system 16 of the teleoperated medical system 10. In other implementations, the visual notification may occur elsewhere, such as on a supplemental display viewed by assistants or clinicians. In some implementations, alerting a healthcare provider may include activating an audible or tactile signal that may communicate to the healthcare provider that an arcing event has occurred. The alert may include any details of the arcing event that may be important. For example, the alert may include details relating to the temperature of tissue affected by the arcing event. The healthcare provider may then take action to minimize additional arcing events from occurring or to otherwise minimize trauma of the tissue at the arcing event. In some instances, the alert is generated only when the temperature exceeds a preset threshold temperature.

Any reference to surgical instruments and surgical methods is non-limiting as the instruments and methods described herein may be used for animals, human cadavers, animal cadavers, portions of human or animal anatomy, non-surgical diagnosis, industrial systems, and general robotic or teleoperational systems.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the invention should be limited only by the following claims, and it is appropriate that the claims be construed broadly and in a manner consistent with the scope of the embodiments disclosed herein.

What is claimed is:

1. A method of detecting an arc during an electrocautery surgical procedure comprising:
viewing an electrosurgical treatment instrument having an electrocautery distal tip and a surgical site with a surgical camera having a surgical field-of-view including the surgical site; and
viewing a portion of the electrosurgical treatment instrument with an electrocautery arc detection system for detecting thermal infrared emission or tissue color changes, the electrocautery arc detection system including an arc detection camera having an arc detection field-of-view different than the surgical field-of-view obtained by the surgical camera.

2. The method of claim 1, wherein viewing the portion of the electrosurgical treatment instrument with the electrocautery arc detection system comprises viewing a shaft portion of the electrosurgical treatment instrument with the arc detection camera.

3. The method of claim 1, wherein the arc detection field-of-view of the arc detection camera is more expansive than the surgical field-of-view of the surgical camera.

4. The method of claim 1, comprising filtering imagery with the electrocautery arc detection system to filter out light having a wavelength not matching a wavelength of light from an electrocautery event.

5. The method of claim 1, comprising filtering imagery with the electrocautery arc detection system to filter out wavelengths of bands of light emitted by a surgical light source.

6. The method of claim 1, comprising introducing a cannula to a patient with the arc detection camera disposed therein; and inserting the electrosurgical treatment instrument through the cannula.

7. The method of claim 1, comprising introducing both the electrosurgical treatment instrument and the surgical camera through an access cannula.

8. The method of claim 1, comprising introducing the arc detection camera to the surgical site from a location that places the surgical camera in the arc detection field-of-view of the arc detection camera.

9. The method of claim 1, wherein the arc detection camera is an infrared thermal imaging camera.

10. The method of claim 9, comprising detecting increases in tissue temperatures with the infrared thermal imaging camera.

11. The method of claim 1, comprising identifying changes in color of a video stream to identify when an arcing event occurs.

12. A method of detecting an arc during an electrocautery surgical procedure comprising:
introducing an electrosurgical treatment instrument to a surgical site, the electrosurgical treatment instrument having an electrocautery tip configured to perform the surgical procedure and a shaft portion supporting the electrocautery tip;
displaying a surgical video stream from a surgical camera assembly having a first field-of-view of the surgical site, the surgical video stream including an image of the electrocautery tip; and
monitoring an arc detecting video stream from an arc detection camera having a second field-of-view larger than the first field-of-view, the arc detection camera being disposed to view portions of the electrosurgical treatment instrument not visible in the first field-of-view.

13. The method of claim 12, wherein monitoring the arc detecting video stream includes filtering the arc detecting video stream to block light wavelengths emitted from a surgical light source.

14. The method of claim 12, wherein monitoring the arc detecting video stream includes automatically detecting an arcing event in the second field-of-view with the arc detecting camera.

15. The method of claim 14, wherein automatically detecting the arcing event in the second field-of-view includes detecting a color change in tissue at the surgical site.

16. The method of claim 14, wherein automatically detecting the arcing event in the second field-of-view includes detecting a flash of light.

17. A system for detecting an arc during an electrocautery surgical procedure at a surgical site comprising:
an electrosurgical treatment instrument having a working tip configured to perform the surgical procedure;
a surgical camera having a field-of-view of the surgical site;
an arc detecting camera having a field-of-view different than the field-of-view of the surgical camera; and
an image processing controller configured to receive information from the arc detecting camera and, based on the information, configured to detect the arc during the electrocautery surgical procedure.

18. The system of claim 17, wherein the arc detecting camera comprises sensors and optics suited for visualizing thermal infrared emissions.

19. The system of claim 18, wherein the sensors and optics comprise HgCdTe-based photosensors and ZnSe optics for visualizing the thermal infrared emissions.

20. The system of claim 17, wherein the arc detecting camera comprises image filtering functionality for filtering light emitted from a surgical light source.

* * * * *